United States Patent
Ueno et al.

(10) Patent No.: US 7,828,723 B2
(45) Date of Patent: Nov. 9, 2010

(54) POWER DRIVEN BENDING ENDOSCOPE WITH DETACHABLE INSERTION PORTION

(75) Inventors: Haruhiko Ueno, Akiruno (JP); Yuichi Ikeda, Tama (JP); Tatsuya Ishizuka, Hachioji (JP); Tatsuya Furukawa, Hachioji (JP); Yutaka Masaki, Mitaka (JP); Masanobu Koitabashi, Hachioji (JP); Noriaki Kanazawa, Musashino (JP)

(73) Assignee: Olympus Corporation, Tokyo (JP)

( * ) Notice: Subject to any disclaimer, the term of this patent is extended or adjusted under 35 U.S.C. 154(b) by 474 days.

(21) Appl. No.: 11/809,849

(22) Filed: Jun. 1, 2007

(65) Prior Publication Data

US 2007/0238927 A1    Oct. 11, 2007

Related U.S. Application Data

(63) Continuation of application No. PCT/JP2005/022197, filed on Dec. 2, 2005.

(30) Foreign Application Priority Data

Dec. 3, 2004 (JP) ............... 2004-351802
Dec. 14, 2004 (JP) ............... 2004-361840

(51) Int. Cl.
*A61B 1/00* (2006.01)

(52) U.S. Cl. ............ 600/136; 600/152; 600/145; 600/146

(58) Field of Classification Search ......... 600/101–102, 600/117–118, 132, 136, 139, 145–146, 152
See application file for complete search history.

(56) References Cited

U.S. PATENT DOCUMENTS

| 4,982,725 | A | | 1/1991 | Hibino et al. |
|---|---|---|---|---|
| 5,447,148 | A | | 9/1995 | Oneda et al. |
| 5,658,238 | A | * | 8/1997 | Suzuki et al. ............... 600/150 |
| 5,888,191 | A | | 3/1999 | Akiba et al. |
| 5,891,014 | A | | 4/1999 | Akiba |
| 6,554,766 | B2 | * | 4/2003 | Maeda et al. ............... 600/132 |
| 6,932,761 | B2 | * | 8/2005 | Maeda et al. ............... 600/152 |
| 7,008,376 | B2 | * | 3/2006 | Ikeda et al. ............... 600/152 |
| 7,331,924 | B2 | * | 2/2008 | Arai et al. ............... 600/145 |
| 2002/0103418 | A1 | | 8/2002 | Maeda |
| 2002/0165432 | A1 | * | 11/2002 | Matsui ............... 600/145 |
| 2003/0009441 | A1 | * | 1/2003 | Holsten et al. ............... 707/1 |
| 2004/0073083 | A1 | * | 4/2004 | Ikeda et al. ............... 600/101 |
| 2004/0073084 | A1 | * | 4/2004 | Maeda et al. ............... 600/101 |
| 2004/0073085 | A1 | | 4/2004 | Ikeda et al. |
| 2004/0193015 | A1 | * | 9/2004 | Ikeda et al. ............... 600/146 |

FOREIGN PATENT DOCUMENTS

| JP | 04-158827 | 6/1992 |
|---|---|---|
| JP | 06-105800 | 4/1994 |

(Continued)

*Primary Examiner*—John P Leubecker
*Assistant Examiner*—Samuel Candler
(74) *Attorney, Agent, or Firm*—Scully, Scott, Murphy & Presser, P.C.

(57) ABSTRACT

A power driven bending endoscope with detachable insertion portion 2 is formed of an insertion body 3 having a flexible bending portion 3B, and a motor unit 4 having an electric motor 23 for driving to bend the bending portion 3B and a potentiometer 26 for detecting a bending state of the bending portion 3B, which are detachably coupled.

3 Claims, 11 Drawing Sheets

FOREIGN PATENT DOCUMENTS

| | | |
|---|---|---|
| JP | 06-114001 | 4/1994 |
| JP | 06-217928 | 8/1994 |
| JP | 06-269398 | 9/1994 |
| JP | 11-032988 | 2/1999 |
| JP | 2003-275168 | 9/2003 |
| JP | 2004121413 A * | 4/2004 |
| JP | 2004174225 A * | 6/2004 |

* cited by examiner

POWER DRIVEN BENDING ENDOSCOPE WITH DETACHABLE INSERTION PORTION

CROSS REFERENCE TO RELATED APPLICATION

This application is a continuation application of PCT/JP2005/022197 filed on Dec. 2, 2005 and claims the benefit of Japanese Application No. 2004-351802 filed in Japan on Dec. 3, 2004 and No. 2004-361840 filed in Japan on Dec. 14, 2004, the entire contents of each of which are incorporated herein by their reference.

BACKGROUND OF THE INVENTION

1. Field of the Invention

The present invention relates to a power driven bending endoscope with detachable insertion portion provided with an insertion body with a bending portion and a power unit equipped with bending drive means for electrically bending the bending portion, which are detachably coupled.

2. Description of the Related Art

Conventionally, the endoscope has been widely used. The insertion portion of the endoscope is inserted into a body cavity such that the inside of the body cavity is observed. The treatment instrument is inserted into the channel for accommodating the treatment instrument formed in the insertion portion to perform various kinds of therapy and treatment.

Generally, the endoscope having the thin and long insertion portion includes a bending portion provided to the leading end of the insertion portion. The bending portion is structured to rotatably connect a plurality of bending pieces. The bending piece which forms the bending portion is connected to the operation wire. The bending portion is vertically or laterally bent by pulling or loosening the operation wire. The operation wire may be pulled or loosened through rotating operation of the bending knob formed on the operation portion performed by the operator, for example.

Recently, the power driven bending endoscope has been introduced, which is structured to bend the bending portion by pulling and loosening the operation wire using the bending drive means such as the electric motor. In the power driven bending endoscope, the electric motor is operated in accordance with the bending command signal outputted from the bending command means, for example, the joystick formed on the operation portion. The rotation of the electric motor is transmitted to the pulley, for example, so as to be rotated. The bending wire wound around the pulley is pulled or loosened to bend the bending portion.

Japanese Unexamined Patent Application Publication No. 2003-275168 discloses the electric flexible endoscope system equipped with the electric flexible endoscope as the aforementioned power driven bending endoscope, which includes predetermined bending detection means for detecting whether the bending portion is at least in one bending state, and predetermined bending informing means for informing that the bending portion becomes the predetermined bending state based on the detection results of the predetermined bending detection means. In addition, the publication discloses, as the predetermined bending detection means, a potentiometer provided in the operation portion of the endoscope.

The electric flexible endoscope system informs the operator that the bending state of the bending portion becomes the predetermined bending state.

Japanese Unexamined Patent Application Publication No. 6-105800 discloses the endoscope device which includes the endoscope device includes the encoder for controlling the rotating speed or the rotating amount of the electric motor. The endoscope device is structured to couple the connector with the connector bearing for guiding the power transmission output portion at the drive side provided at the enclosure of the bending motor controller and the connector at the input side formed in the connector of the endoscope to the predetermined coupled position.

In the aforementioned power driven bending endoscope, the power unit provided outside the operation portion to serve as the bending drive means is detachable with respect to the endoscope, reducing the size and weight of the operation portion and improving the operability.

The endoscope device disclosed in Japanese Unexamined Patent Application Publication No. 6-114001 includes a guide portion at the first joint portion disposed in the endoscope, and a guided portion at the second joint portion disposed inside the enclosure in the bending controller as the power unit. In the case where the first and the second joint portions are eccentrically connected with respect to the respective center axes, they may be coaxially connected by means of the guide portion and the guided portion.

SUMMARY OF THE INVENTION

The power driven bending endoscope with detachable insertion portion according to the present invention is formed of the insertion body including a flexible bending portion and the power unit equipped with the bending drive unit for driving to bend the bending portion and the bending state detection unit for detecting the bending state of the bending portion, which are detachably coupled.

DETAILED DESCRIPTION OF THE PREFERRED EMBODIMENT(S)

Figure 1:
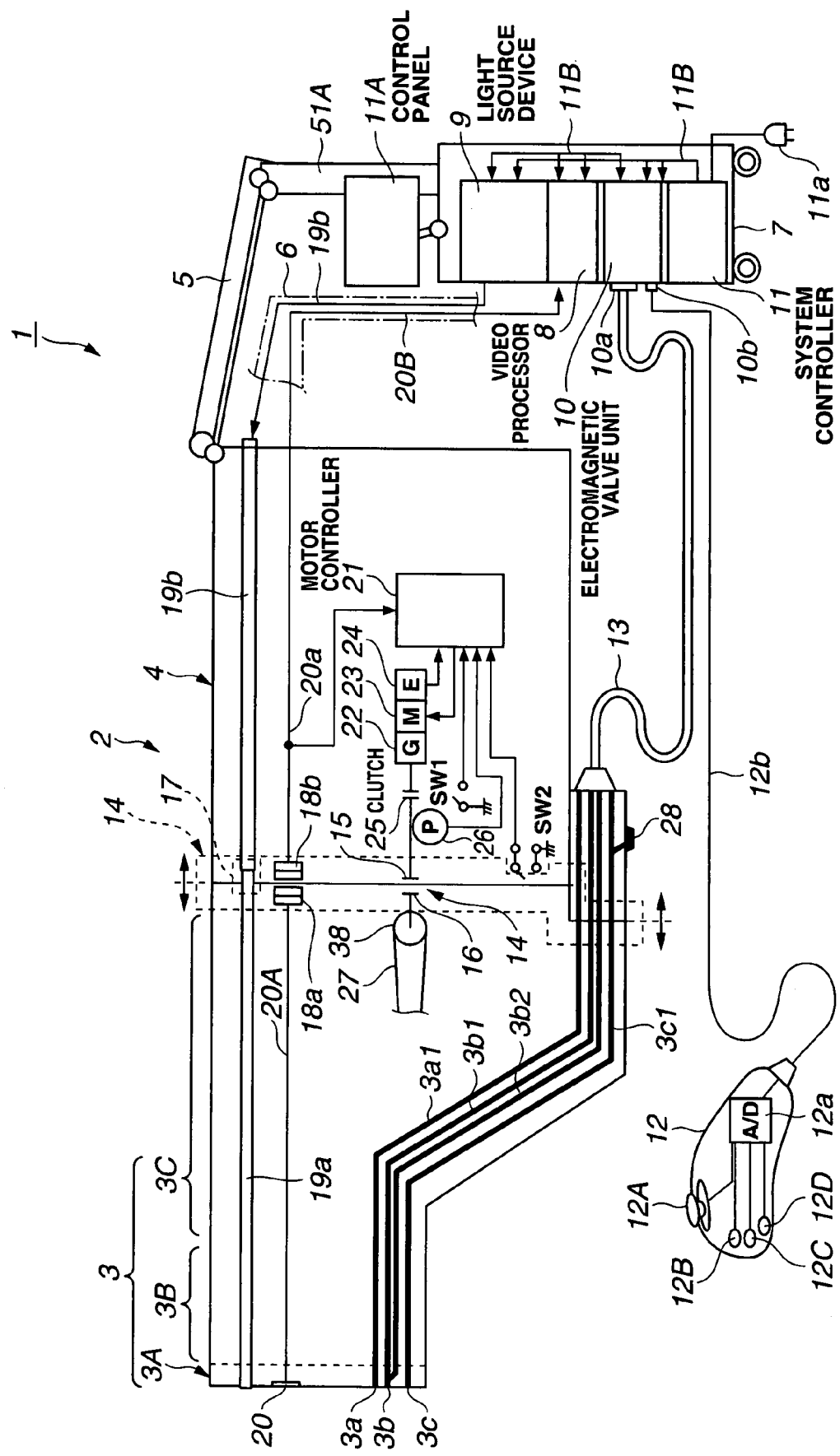
FIG. 1 is an explanatory view showing a structure of the endoscope system equipped with the power driven bending endoscope with detachable insertion portion.

An embodiment according to the present invention will be described referring to the drawings.

Embodiment 1 according to the present invention will be described referring to FIGS. 1 to 5.

Figure 2:
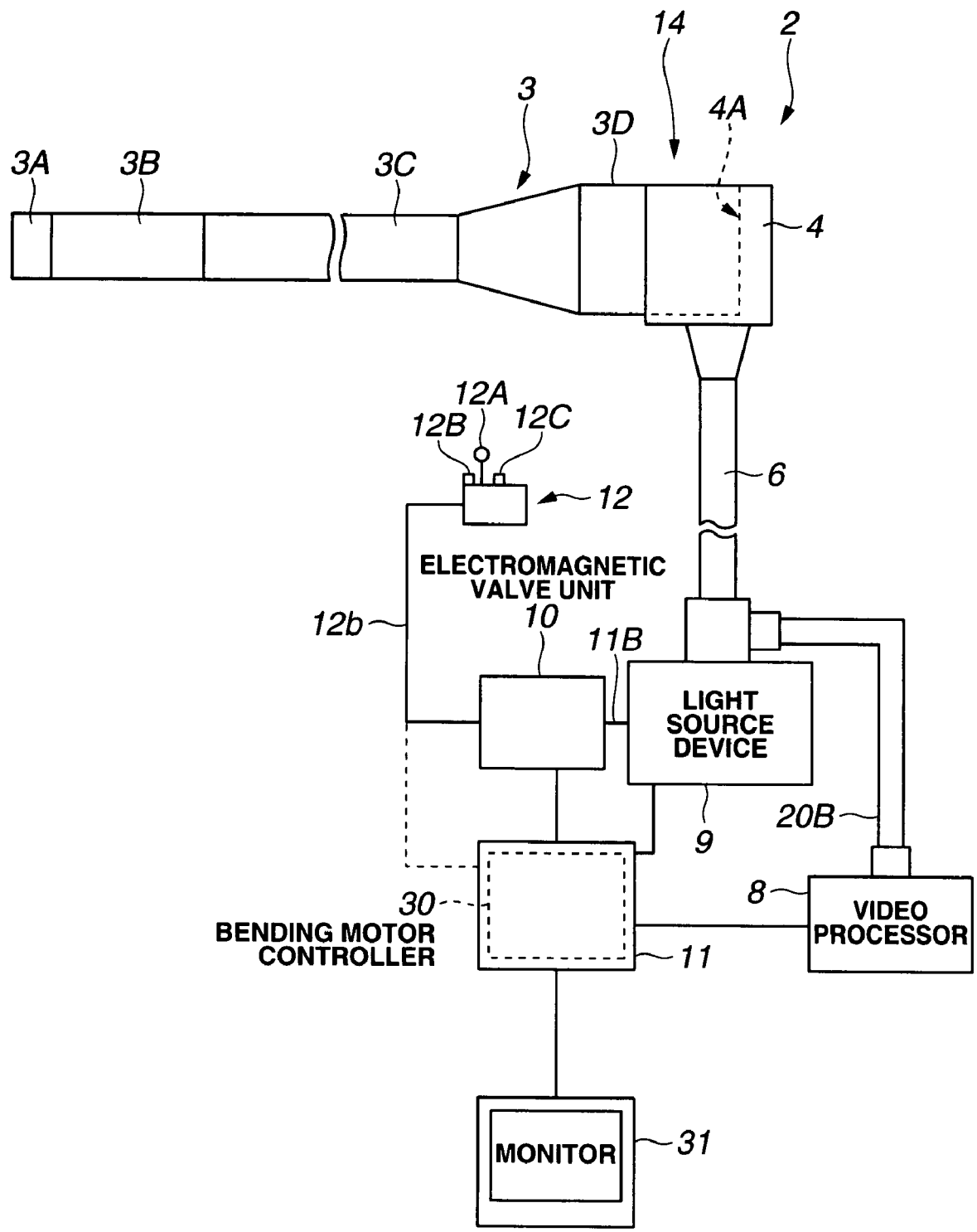
FIG. 2 is an explanatory view showing a connection between the power driven bending endoscope with detachable insertion portion and the external devices.

Referring to FIGS. 1 and 2, an endoscope system 1 is formed of a power driven bending endoscope with detachable insertion portion (hereinafter referred to as the endoscope) 2 and external devices.

The endoscope 2 is mainly formed of an insertion body 3 and a motor unit 4 as a power unit. The motor unit 4 and the insertion body 3 are detachably coupled as described later.

The insertion body 3 includes a distal rigid portion 3A, a bending portion 3B, a flexible tube 3C, an insertion portion engagement portion 3D arranged in the order from the leading end. The distal rigid portion 3A contains an image pickup device 20, for example. The bending portion 3B is bent by pulling or loosening an angle wire 27. In the case where the bending portion 3B is bent both in the vertical and lateral directions, a pair of angle wires 27 are provided. The explanation herein will be made using only a single angle wire 27 as shown in FIG. 1.

The endoscope 2 is movably held by a scope holder 5 having a motor unit 4 detachably connected to the distal end. The proximal end of the scope holder 5 is attached to the upper portion of the cart 7. The external devices including a video processor 8, a light source device 9, an electromagnetic valve unit 10, and a system controller 11 are mounted on the cart 7.

A signal cable 20B is connected to the video processor 8 which generates the video signal from the electric signal transferred from the image pickup device 20 through the signal cables 20A, 20a and 20B. The video signals generated in the video processor 8 are outputted to a monitor 31 and the like as the display unit such that the endoscope image is displayed on the display of the monitor 31.

The light source device 9 supplies illuminating light to an illuminating optical system of the endoscope 2. Specifically, the illuminating light is transmitted through the universal cord 6, a light guide fiber 19b inserted through the motor unit 4, and a light guide fiber 19a in the insertion body 3.

The electromagnetic valve unit 10 is a conduit controller, to which a signal cable 12b extending from an operation portion 12 described later and tubes 13 are connected. The electromagnetic valve unit 10 controls air supply, water supply or suction through the tubes 13, and a front water supply conduit 3a1, an air supply conduit 3b1, a water supply conduit 3b2, and a suction conduit 3c1 also serving as a forceps conduit provided in the insertion body 3.

The system controller 11 controls a motor signal controller (hereinafter referred to as a motor controller) 21 provided in the motor unit 4, and executes the entire control of the system including the video processor 8, the light source device 9, and the electromagnetic valve unit 10. The motor controller 21 serving as the control means generates the motor drive signal for driving the electric motor 23. The electric motor 23 serving as the bending drive means generates the driving force to pull and loosen the angle wire 27. The system controller 11 is electrically coupled with a control panel 11A. The operation portion provided on the display of the control panel 11A is used to give various types of operation command to the respective devices.

The operation portion 12 serves as operation means, and outputs such command signals as the bending command signal for bending the bending portion 3B which forms the insertion body 3, a command signal for air supply, a command signal for water supply, or a command signal for suction.

The insertion body 3 and the motor unit 4 are detachably coupled via a detaching portion 14 as the detaching means. The detaching portion 14 is provided with engagement means which enables the engagement at a predetermined position. The engagement means is structured to include the first and the second power transmission portions for transmitting the power from the motor unit 4 to the pulling means of the bending portion 3B of the insertion body 3. In the embodiment, the pulling means is as, for example, the sprocket as described later.

Clutch portions 15 and 16 formed at the detaching portion 14 are specifically dock clutch portions at the endoscope (hereinafter referred to as the endoscope clutch portion) formed on the insertion body 3 as the first power transmission unit 16, and a dock clutch portion 15 as the second drive transmission portion formed on the motor unit 4 (hereinafter referred to as the motor clutch portion). The endoscope clutch portion 16 and the motor clutch portion 15 are engaged always at the constant position. The separation structure of the insertion body 3 and the motor unit 4 including the detaching portion 14 will further be described later in more detail.

A light guide fiber 19a is provided in the insertion body 3, and the light guide fiber 19b is provided in the motor unit 4. The light guide fibers 19a and 19b are detachable by an optical connector 17 so as to be detachable accompanied with the detachment of the insertion body 3 and the motor unit 4. When the insertion body 3 is coupled with the motor unit 4, the optical connector 17 which has been in the separated state is brought into the attachment state such that the illuminating light is transmitted. The universal cord 6 is provided to the proximal end portion of the motor unit 4. The light guide fiber 19b is inserted to the inside of the universal cord 6.

The signal cable 20A extends from the image pickup device 20. An electric connector 18a is provided to the detaching portion 14 at the insertion body 3 side as the proximal end of the signal cable 20A. Meanwhile, an electric connector 18b is provided to the detaching portion 14 at the motor unit 4 side. The electric connector 18b is connected to the signal cable 20a. The electric connectors 18a and 18b are structured to be detachable.

When the insertion body 3 and the motor unit 4 are coupled, those two electric connectors 18a and 18b are electrically coupled, and accordingly, the signal cables 20A and the 20a are electrically coupled.

The proximal end of the signal cable 20a is connected to the signal cable 20B disposed in the universal cord 6. Accordingly, the image pickup device 20 is electrically coupled with the video processor 8 via the signal cable 20A, the electric connectors 18a, 18b, the signal cable 20a, and the signal cable 20B.

A front water supply opening 3a, an air/water supply opening 3b, and a suction opening 3c are formed in the distal end surface of the distal rigid portion 3A which forms the insertion body 3. Those openings are communicated with conduits 3a1, 3b1, 3b2, and 3c1 disposed in the insertion body 3. The conduits 3a1, 3b1, 3b2 and 3c1 are separated into parts corresponding to the insertion body 3 side and the motor unit 4 side, respectively. The separated conduits 3a1, 3b1, 3b2 and 3c1 are fluid tightly coupled upon assembly of the insertion body 3 and the motor unit 4. Each end of the respective conduits at the motor unit 4 side is connected to the corresponding end portion of the tube. Each proximal end of the tubes is connected to a fluid connector 10a of the electromagnetic valve unit 10.

A forceps insertion opening 28 communicated with the suction conduit 3c1 is formed in the motor unit 4. The treatment instrument such as the forceps is inserted into the suction conduit 3c1 through the forceps insertion opening 28 to guide the forceps through the suction opening 3c so as to perform the treatment.

The signal cable 20a connected to the electric connector 18b is electrically coupled with the motor controller 21 disposed in the motor unit 4. As the operator operates the operation portion 12, the system controller 11 generates the bending operation signal corresponding to the operation of the operation portion 12. The bending operation signal generated by the system controller 11 is inputted to the motor controller 21 via the signal cables 20B and 20a.

The motor unit 4 includes the aforementioned electric connector 18b, the motor controller 21, the electric motor 23, the encoder 24 and the potentiometer 26, the reduction gear 22, the electromagnetic clutch 25, the switch (SW) 1 and the switch (SW) 2.

The motor controller 21 controls the driving operation of the electric motor 23. The encoder 24 serving as the driving state detection means brings the operation state of the electric motor 23, for example, the rotating speed and the rotating amount into data so as to be outputted to the motor controller 21. That is, the rotating amount and the like of the electric motor 23 is detected by the encoder 24, and the detection results are outputted to the motor controller 21. The potentiometer 26 serving as the bending state detection means detects the rotating amount of the sprocket 38 based on the rotation of the motor clutch portion 15 engaged with the endoscope clutch portion 16 which integrally rotates with the sprocket 38. The detection results are outputted to the motor controller 21. The reduction gear 22 reduces the rotating driving force of the electric motor 23. The electromagnetic clutch 25 is linked with the reduction gear 22, and switches the transmission of the rotating power to the insertion body 3. The switch (SW1) detects whether the electromagnetic clutch 25 is in the power transmission state or the power transmission disconnection state. The switch (SW2) detects whether or not the insertion body 3 and the motor unit 4 are in the coupled state.

The bending operation signal generated by the system controller 11 is inputted to the motor controller 21 based on the command signal outputted from the operation portion 12. The motor controller 21 then generates the motor drive signal to drive the electric motor 23. Based on the detection results outputted from the encoder 24 and the detection results outputted from the potentiometer 26, the motor controller 21 generates the motor drive signal corresponding to the bending operation signal to control the driving operation of the electric motor 23. The bending portion 3B is bent under the driving force applied from the electric motor 23.

Specifically, the rotating driving force of the electric motor 23 is transmitted to the sprocket 38 via the motor clutch portion 15 and the endoscope clutch portion 16 of the detaching portion 14. A chain 37 (see FIG. 6) connected to the angle wire 27 is wound around the sprocket 38. Accordingly, when the driving force is transmitted to the sprocket 38 to be rotated in the predetermined direction, the chain 37 is moved accompanied with the rotation of the sprocket 38. The angle wire 27 then moves forward and rearward such that the bending portion 3B is bent.

The operation portion 12 includes a joystick 12A as an operation switch, and buttons 12B, 12C, 12D and 12E for controlling the fluid. The joystick 12A is used for commanding the bending operation in the vertical and lateral directions of the bending portion 3B. The button 12B is a two-staged air/water supply button, for example, for commanding the air supply at the first stage, and commanding the water supply at the second stage. The button 12C is a suction button which is operated to command the suction. The button 12D as a front water supply button is operated to command the forward water supply.

The operation portion 12 contains an A/D convertor 12a therein. The A/D convertor 12a is electrically coupled with the respective operation switches 12A, 12B, 12C and 12D. The A/D converter 12a converts the operation commands from the respective operation switches 12A, 12B, 12C and 12D into the electric signals so as to be outputted to the electromagnetic valve unit 10 via the signal cable 12b and the connector 10b as the operation command signals.

The medical equipment such as the video processor 8, the light source device 9 and the electromagnetic valve unit 10 is connected to the system controller 11 via the communication cable 11B. Therefore, the operation command of the joy stick 12A is inputted from the electromagnetic valve unit 10 to the system controller 11 via the communication cable 11B. Accordingly, the electromagnetic valve unit 10 is controlled based on the various operation signals of the system controller 11. The system controller 11 may be operated through the control panel 11A of touch panel type, the operation portion 12, or the remote controller (not shown). The control operation of the system controller 11 may be displayed on the control panel 11A or the monitor 31.

Referring to FIG. 2, the system controller 11 includes a bending motor controller 30. The bending motor controller 30 generates the bending operation signal based on the command signal outputted from the operation portion 12 so as to be outputted to the motor controller 21. That is, the bending motor controller 30 outputs the bending operation signal corresponding to the operation command of the joy stick 12A of the operation portion 12 to the motor controller 21. Accordingly, the operation command signal outputted from the operation portion 12 may be transmitted to the bending motor controller 30 of the system controller 11 directly without through the electromagnetic valve unit 10. The signal cable 12b may be connected to the system controller 11 as shown by the broken line.

The separation structure of the insertion body 3 and the motor unit 4 including the clutch portions 15 and 16 of the detaching portion 14 will be described referring to FIG. 3.

Referring to the drawing, the endoscope 2 is provided with the detaching portion 14 for separating the endoscope 2 into the insertion body 3 and the motor unit 4. The motor clutch portion 15 is formed on the motor unit 4, and the endoscope clutch portion 16 is formed on the insertion body 3.

The motor unit 4 includes a recess-like storage portion 4A which forms the detaching portion 14. The storage portion 4A stores main portion of the insertion portion engagement portion 3D of the insertion body 3 which forms the detaching portion 14.

The motor clutch portions 15 are formed on both side wall surfaces, which form the storage portion 4A. Pin guides 33 for guiding the pins 36 as the positioning means formed on the endoscope clutch portions 16 to be described later are formed on both side wall surfaces to the front of the motor clutch portion 15.

The motor clutch portion 15 includes a plurality of protrusions 15a and recesses 15b alternately arranged along the rotating shaft in the radial direction so as to be engaged with the endoscope clutch portion 16 (described later). One of the plurality of recesses 15b includes an engagement groove (see the reference numeral 35 in FIGS. 4 and 5) as the positioning means through which the pin 36 is inserted.

The pin guide 33 is formed of a pair of protrusions 33a. The pin guide 33 includes a guide opening 33A for guiding the pin 36 formed on the endoscope clutch portion 16. The protrusions 33a include guide surfaces 33b for smoothly guiding the contacted pin 36 to the guide opening 33A. The guide surface 33b is formed as the curved surface or the tilted surface.

An electric contact 4B serving as the electric connector 18b and an optical connector 17a at one side of the optical connector 17 (not shown) are formed in the back wall surface of the storage portion 4A. In the state where the insertion body 3 is stored in the storage portion 4A, the electric contact 4B is brought into contact with an electric contact 3E formed on the proximal end surface of the insertion body 3 corresponding to the electric connector 18a so as to be conducted. The connector 17a at the motor side is brought into contact with the connector 17b at the endoscope side formed on the proximal end of the insertion body 3 so as to be in the illumination light transmission state.

Engagement/disengagement buttons 34 are formed in the outer surface of the side wall surfaces of the motor unit 4 for switching the engagement/disengagement state between the motor clutch portion 15 and the endoscope clutch portion 16.

Figure 6:
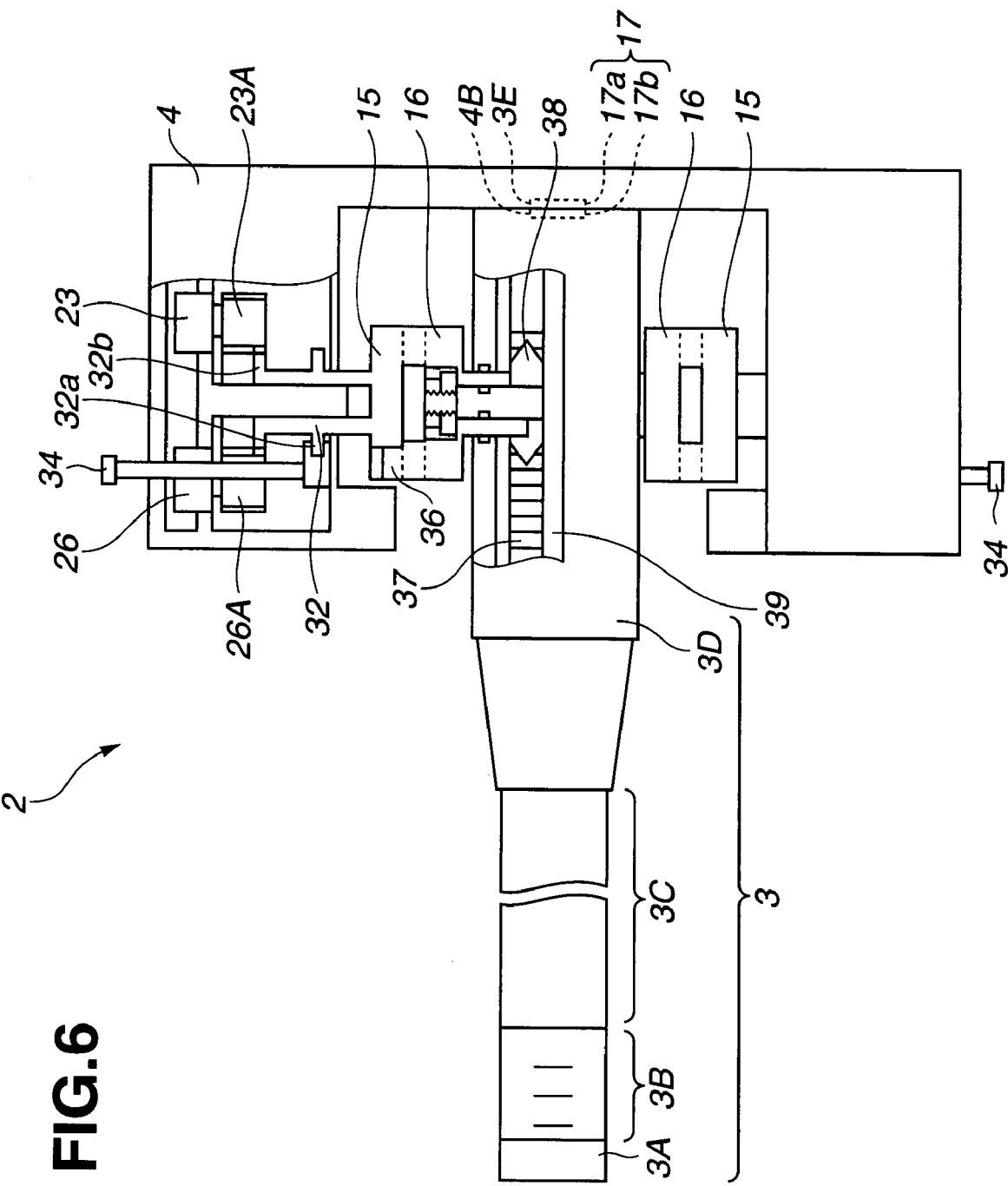
FIG. 6 is an explanatory view showing the endoscope having the endoscope body coupled with the motor unit.

Referring to FIG. 6, the distal end portion of the engagement/disengagement button 34 is engaged with a protrusion 32a provided onto the shaft 32 of the motor clutch portion 15. The shaft 32 of the motor clutch portion 15 is movable with respect to the motor unit 4. The shaft 32 moves in the direction orthogonal to the longitudinal axial direction of the insertion body 3 which has been assembled. That is, as the engagement/disengagement button 34 is operated, the motor clutch portion 15 moves in the direction orthogonal to the longitudinal axial direction of the insertion body 3.

Meanwhile, the endoscope clutch portions 16 are provided at both sides of the insertion portion engagement portion 3D which form the insertion body 3. A plurality of recesses 16b and protrusions 16a are alternately arranged in the radial direction along the rotating shaft on the clutch portions 16 at the endoscope side, which are brought into engagement with the plurality of the protrusions 15a and the recesses 15b, respectively. A pin 36 is provided on the surface of one of the plurality of protrusions 16a, which protrudes perpendicular to the surface thereof.

In the endoscope 2 according to the embodiment, the pin 36 is provided on the endoscope clutch portion 16, and the pin guide 33 is provided at the motor unit 4. Thus, upon formation of the endoscope 2 by coupling the insertion body 3 and the motor unit 4, the positional relationship of the engagement state between the motor clutch portion 15 and the endoscope clutch portion 16 may be constantly kept.

In the endoscope 2 of the embodiment, the motor unit 4 is provided with the encoder 24 and the potentiometer 26 in the state where the insertion body 3 and the motor unit 4 are separated. In the aforementioned state, the insertion body 3 may be subjected to the autoclave sterilization.

The motor unit 4 is provided with the encoder 24 and the potentiometer 26 to make it sure to detect the bending state of the bending portion 3B with high accuracy under the bending control.

The motor clutch portion 15 and the endoscope clutch portion 16 are always engaged at a constant positional relationship. Although the motor unit 4 is provided with the potentiometer 26, the rotating amount of the sprocket 38 disposed in the insertion body 3 may be measured by detecting the rotation of one of the clutch portions 15 and 16 which rotates in association with the sprocket 38, that is, the clutch portion 15. In other words, the rotation of the clutch portion 15 is regarded as that of the sprocket 38 so as to detect the bending configuration of the bending portion 3B. The clutch portions 15 and 16 are formed of the dock type clutches to make it sure to transmit the power required for bending the bending portion 3B to the sprocket 38 which allows the electric motor 23 to pull and loosen the angle wire 27 efficiently.

Figure 4:
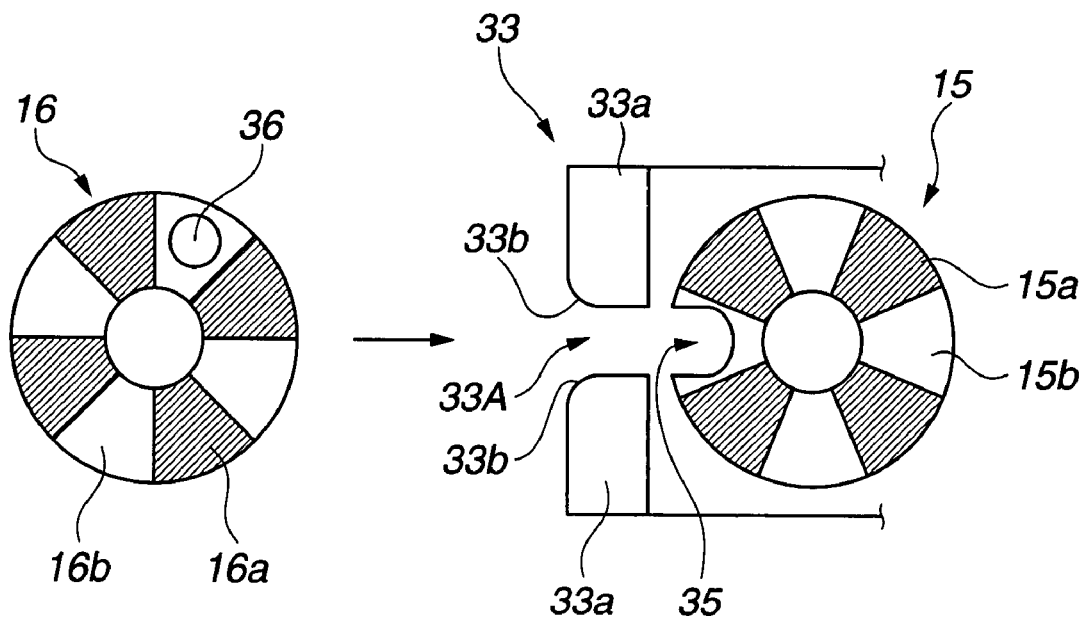
FIG. 4 is an explanatory view showing the state before engagement of the endoscope clutch portion with the motor clutch portion.

The assembly procedure of the endoscope 2 and the function of the endoscope system 1 will be described referring to FIGS. 4 and 6.

Figure 3:
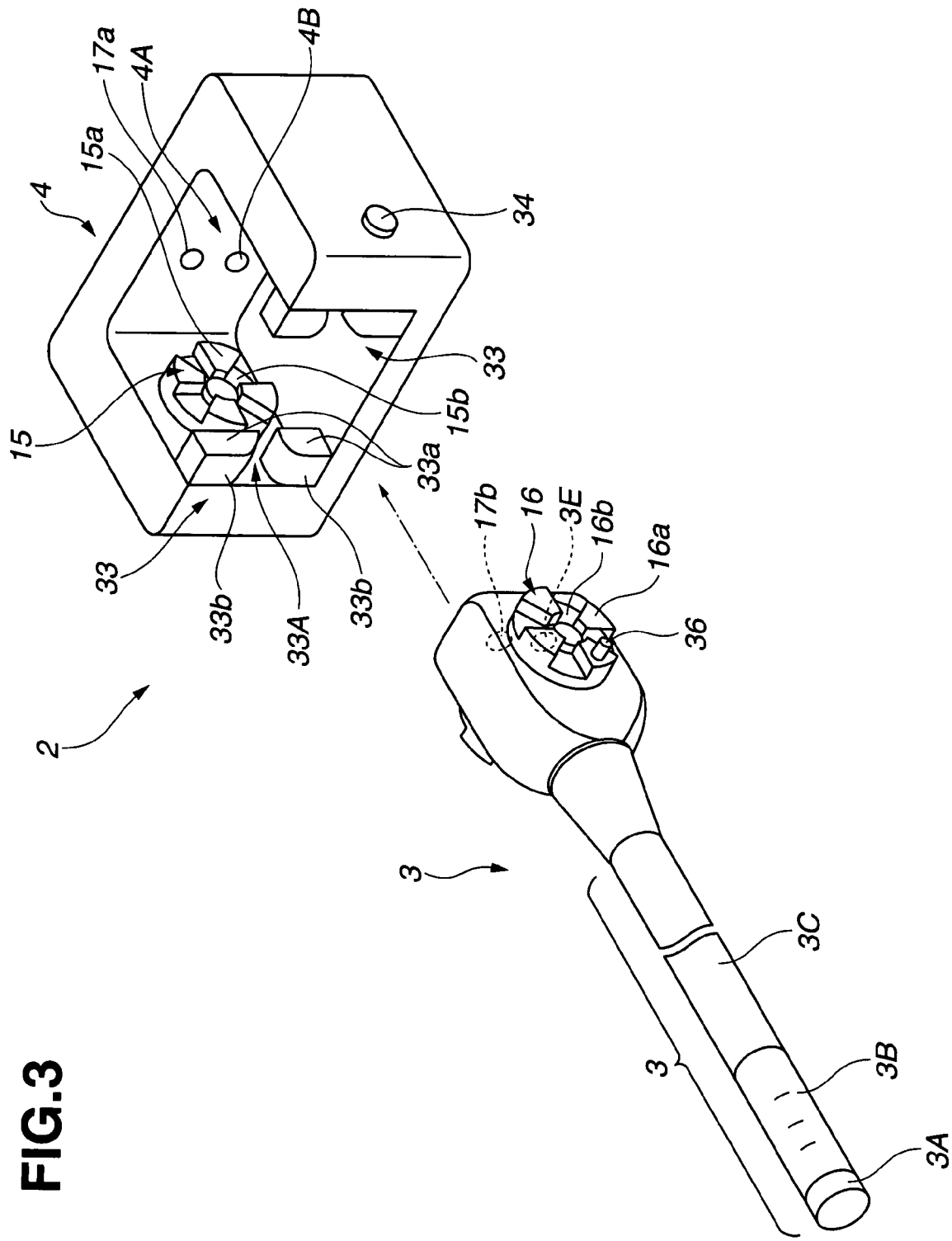
FIG. 3 is an exploded perspective view of the power driven bending endoscope with detachable insertion portion in the state where the insertion body and the motor unit are separated.

Firstly, the operator brings the separated insertion body 3 toward the direction, for example, as shown by the arrow in FIG. 3 for the purpose of assembling the endoscope 2 according to the embodiment until the pin 36 formed in the endoscope clutch 16 abuts against the pin guide 33 formed on the motor unit 4.

Figure 5:
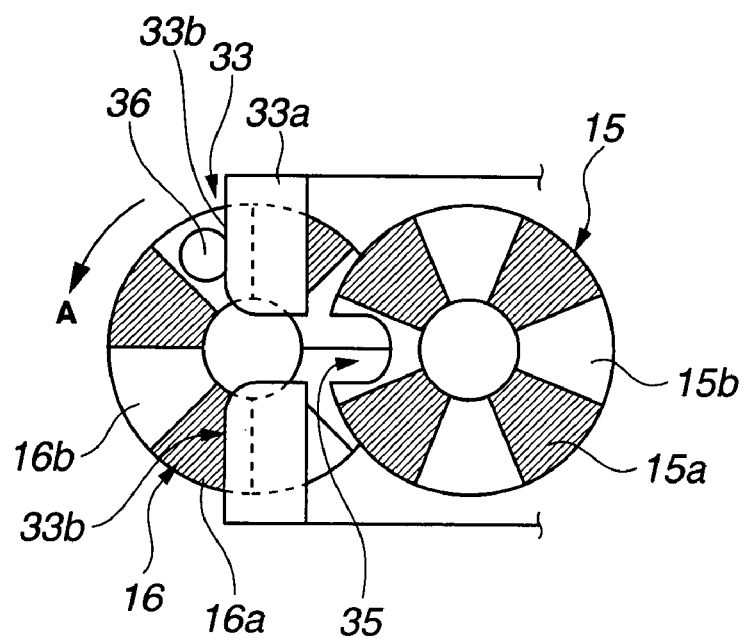
FIG. 5 is an explanatory view showing the state where the pin formed on the endoscope clutch portion abuts against the guide surface of the pin guide.

As the operator further brings the insertion body 3 rightward in the drawing, the endoscope clutch portion 16 integrated with the pin 36 rotates in the direction, for example, as shown by the arrow A in FIG. 5. The pin 36 is guided toward the guide opening 33A along the guide surface 33b of the pin guide 33.

In the state where the pin 36 is positioned at the guide opening 33A, as the operator further brings the insertion body 3 rightward in the drawing, the pin 36 passes over the pin guide 33 to be fit with a fit groove 35 of the motor clutch portion 15. As a result, the motor clutch portion 15 and the endoscope clutch portion 16 are brought into the predetermined engagement state.

In the embodiment, when the stop signal is outputted to the motor controller 21, the fit groove 35 stops at the position opposite the guide opening 33A, or the motor clutch portion 15 is rotated by the operator to bring the fit groove 35 to the position opposite the guide opening 33A.

Next, the operator depresses the respective engagement/disengagement buttons 34 formed on the motor unit 4. As the engagement/disengagement button 34 is depressed, the shaft 32 of the motor clutch portion 15 moves to approach the endoscope clutch portion 16. Then the protrusions 15a and recesses 15b of the motor clutch portion 15 are brought into engagement with the recesses 16b and the protrusions 16a of the endoscope clutch portion 16, respectively. That is, the protrusions 15a of the motor clutch portion 15 mesh with the recesses 16b of the endoscope clutch portion 16, and the recesses 15b of the motor clutch portion 15 mesh with the protrusions 16a of the endoscope clutch portion 16.

The endoscope 2 having the insertion body 3 coupled with the motor unit 4 through engagement between the endoscope clutch portion 16 and the motor clutch portion 15, thus, may be formed as shown in FIG. 6.

In the endoscope 2 shown in FIG. 6, the motor clutch portion 15 is engaged with the endoscope clutch portion 16. Therefore, the rotating power of the electric motor 23 is transmitted to the endoscope clutch portion 16 and the sprocket 38 operated in association therewith via the motor pinion 23A, the gear 32b provided to the shaft 32, and the motor clutch portion 15 (specifically, the reduction gear 22 and the clutch 25 shown in FIG. 1). The sprocket 38 then moves the chain 37 connected to the angle wire 27. The angle wire 27 connected to the chain 37 is pulled or loosened to bend the bending portion 3B.

The gear 32b of the motor clutch portion 15 meshes with the pinion 26A of the potentiometer 26 to detect the rotating amount of the sprocket 38.

The electric contacts 4B and 3E are brought into the electric conductive state, and the motor optical connector 17a and the endoscope optical connector 17b are connected to be ready for transmitting the illuminating light in the state where the insertion body 3 is coupled with the motor unit 4. That is, the electric contact 3E of the insertion body 3 and the endoscope optical connector 17b, and the electric contact 4B of the motor unit 4 and the motor optical connector 17a are connected simultaneously.

As the electric contacts 3E and 4B are electrically coupled, the image pickup device 20 and the video processor 8 are electrically coupled to be ready for transmitting the drive signal and the video signal. During the observation with the endoscope, the video signal picked up by the image pickup device 20 is supplied to the video processor 8 via the signal cable 20A, the electric connectors 18a, 18b, and the signal cables 20a, 20B.

As the endoscope optical connector 17b and the motor optical connector 17a of the optical connector 17 are connected, the illuminating light supplied from the light source device 9 is irradiated to the target observation site via the light guide fiber 19b, the optical connector 17, and the light guide fiber 19a as shown in FIG. 1.

The endoscope clutch portion 16 formed at the insertion portion engagement portion 3D and the motor clutch portion 15 formed on the motor unit 4 at the upper portion in the drawing are formed as the mechanism for bending the bending portion 3B to left and right, for example. Meanwhile, the endoscope clutch portion 16 and the motor clutch portion 15 at the lower portion in the drawing are formed as the mechanism for bending the bending portion 3B up and down.

The procedure for separating the endoscope 2 into the insertion body 3 and the motor unit 4 will be described.

The operator stops the electric motor 23 for the purpose of separating the endoscope 2 into the insertion body 3 and the motor unit 4. In the aforementioned state, the respective engagement/disengagement buttons 34 are returned. As the tip portion of the engagement/disengagement button 34 moves, the shaft 32 of the motor clutch portion 15 moves in the direction away from the endoscope clutch portion 16. As a result, the motor clutch portion 15 is disengaged from the endoscope clutch portion 16. The operator then grasps the insertion body 3 to be brought to the direction reverse of the arrow in the drawing such that the insertion body 3 is removed from the storage portion 4A of the motor unit 4.

At this time, the bending portion 3B is required to be made straight such that the insertion body 3 is disengaged from the motor unit 4. As the bending portion 3B is made straight, the position of the pin 36 coincides with that of the guide opening 33A, which allows the insertion body 3 to be smoothly disengaged from the motor unit 4.

In the embodiment, the engagement/disengagement buttons 34 are provided for the vertical and lateral movements so as to be independently operated. However, one of the engagement/disengagement buttons or a single operation button may be structured to move the motor clutch portion 15. The engagement state and the disengagement state between the motor clutch portion 15 corresponding to the vertical and the lateral movements and the endoscope clutch portion 16 may be switched by operating only the single engagement/disengagement button.

In the embodiment, the switching between the engagement and disengagement states with the engagement/disengagement buttons 34 may be mechanically performed. However, the switching with the engagement/disengagement buttons 34 may be electrically performed.

In the endoscope 2 according to the embodiment, the motor unit 4 structured to be detachably coupled with the insertion body 3 is provided with the encoder 24 and the potentiometer 26. This allows the insertion body 3 to be subjected to the autoclave sterilization.

As the endoscope 2 includes both the encoder 24 and the potentiometer 26, the respective rotations of the electric motor 23 and the sprocket 38 may be detected, and the bending state of the bending portion 3B may also be detected with high accuracy, thus contributing to further improvement of safety in the observation with the endoscope.

The rotating power of the electric motor 23 is transmitted to the sprocket 38 via the clutch portions 15 and 16 to bend the bending portion 3B. This makes it possible to efficiently transmit the power required for rotating the sprocket 38.

The motor clutch portion 15 and the endoscope clutch portion 16 are always engaged at the constant position, which may eliminate the calibration for positioning to restore the intended relationship between the position of the electric motor 23 and the bent state of the bending portion 3B. The insertion body 3 and the motor unit 4, thus, may be easily coupled.

Two engagement/disengagement buttons 34 are described as having the structure to perform the disengagement independently. However, they are not limited to the aforementioned structure. Those two engagement/disengagement buttons 34 may be linked such that the disengagement with respect to both the endoscope clutch portions 16 is performed through a single operation.

Figure 7:
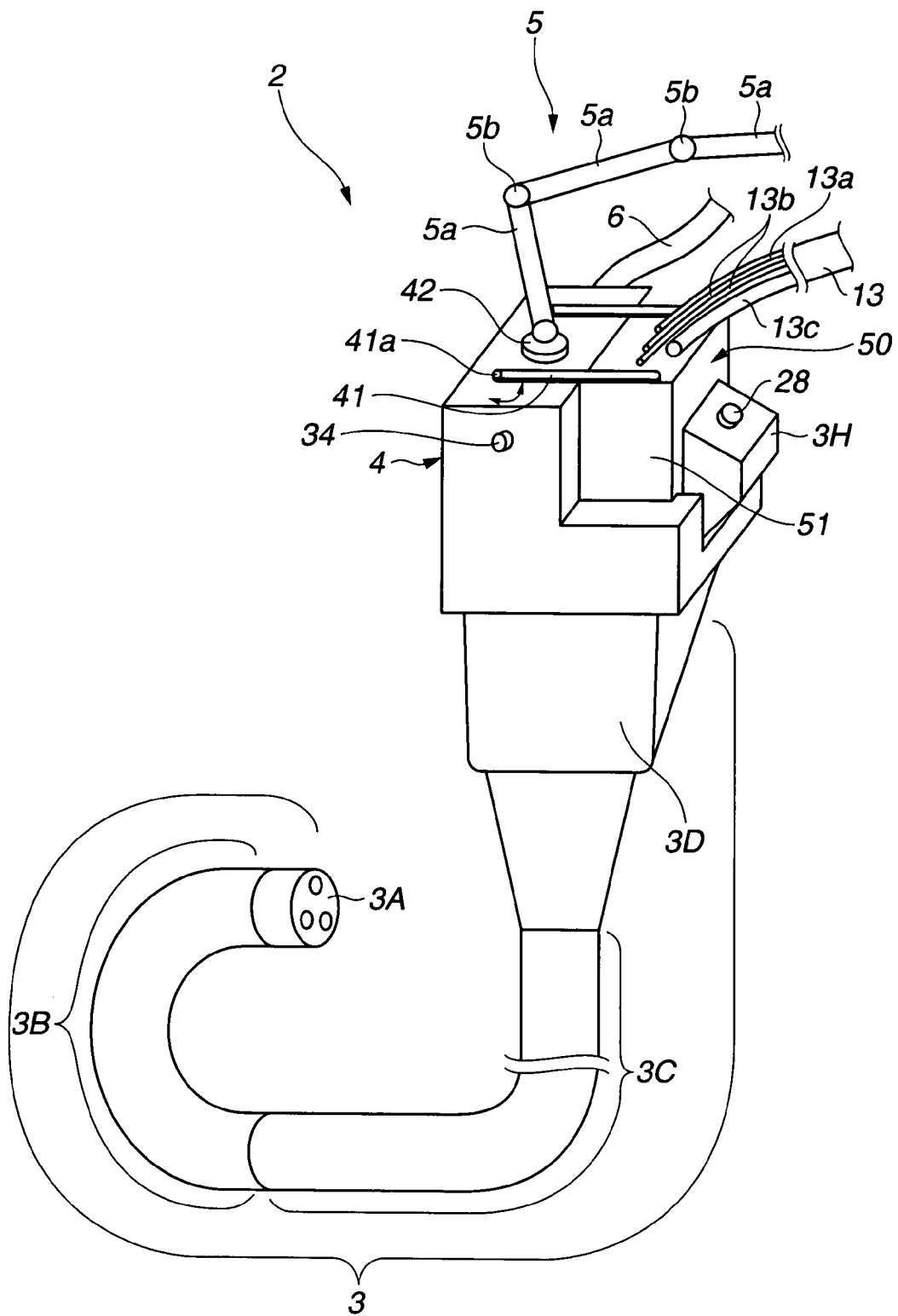
FIG. 7 is an explanatory view showing the endoscope having the endoscope body, the motor unit, and the separative conduit coupled.

Referring to FIG. 7, the endoscope 2 according to the embodiment is detachably formed of the insertion body 3 having the bending portion 3B, the motor unit 4 having the electric motor 23 integrated therewith, and the separative conduit 50 including the tubes 13a, 13b, 13c and 13d to be described later. In the drawing, a scope holder 5 is provided to the proximal end surface of the motor unit 4. The scope holder 5 is formed of a plurality of arm portions 5a and rotative holding members 5b which rotatably hold the arm portions 5a at the rotating positions. Thus, the endoscope 2 may be movably held.

Figure 8:
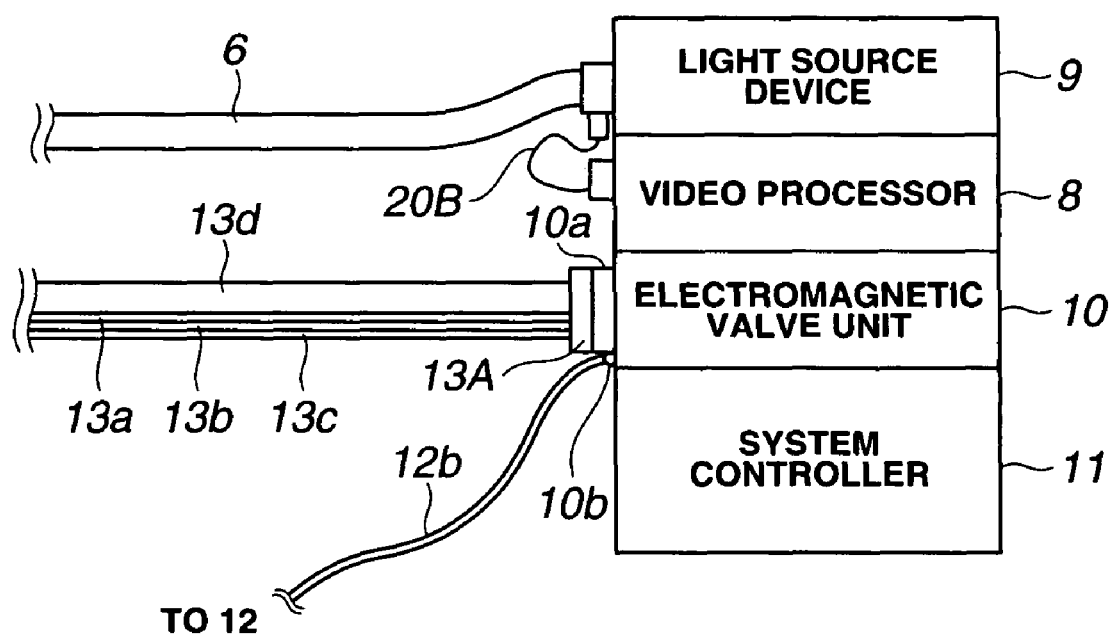
FIG. 8 is an explanatory view showing the state where the various tubes and the universal cords are connected to the external devices.
Figure 11:
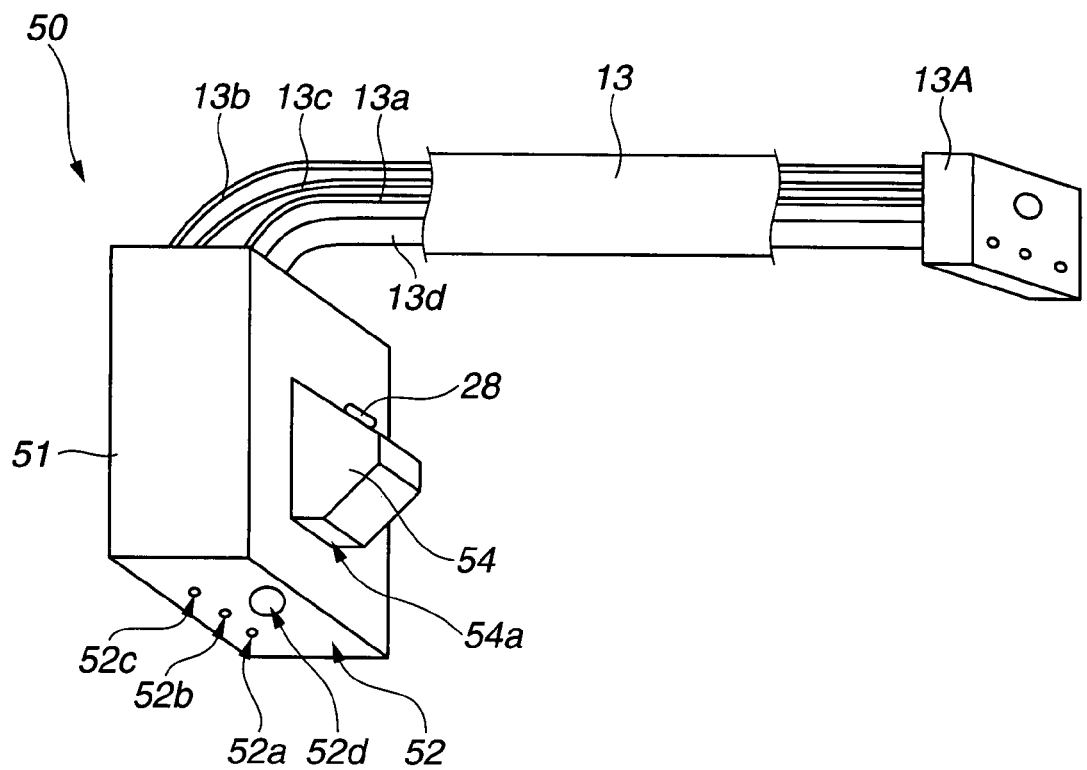
FIG. 11 is an explanatory view showing the entire structure of the separative conduit.
Figure 12:
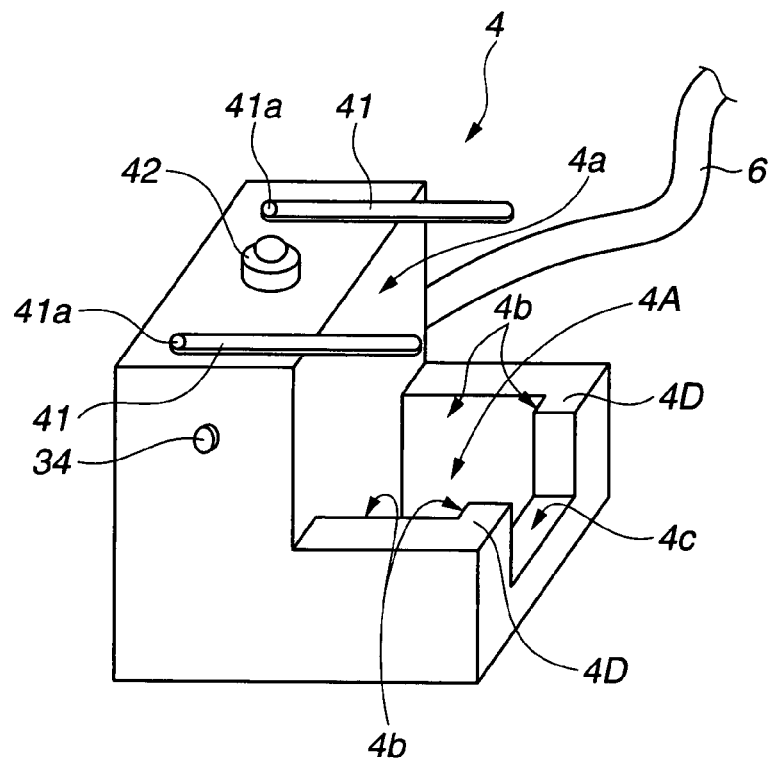
FIG. 12 is a perspective view showing the motor unit in the state where the first storage portion as the tube insertion connector is disposed to the front.
Figure 13:
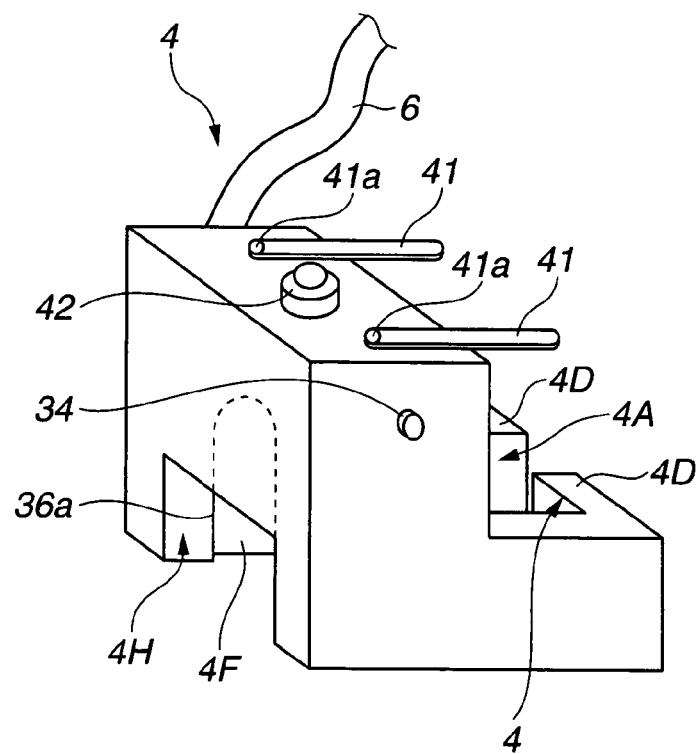
FIG. 13 is a perspective view showing the motor unit in the state where the first storage portion as the tube insertion connector is provided to the rear.

The separative conduit 50 is formed of a tube insertion connector 51, a front water supply tube 13a, an air supply tube 13b, a water supply tube 13c, and a suction tube 13d disposed on the tube insertion connector 51. Each proximal end of the respective tubes 13a, 13b, 13c and 13d is collectively detachable with respect to a fluid connector 10a of the electromagnetic valve unit 10 shown in FIG. 8 via a tube connector 13A as shown in FIG. 11. The universal cord 6 is connected to the light source device 9, the signal cable 20B is connected to the video processor 8, and the signal cable 12b is connected to the connector 10b.

The insertion body 3 which forms the detaching portion 14 is provided with the endoscope clutch portion 16 serving as the engagement means and as the first power transmission portion. The motor unit 4 is provided with the motor clutch portion 15 serving as the engagement means and as the second power transmission portion. The endoscope clutch portion 16 includes an engagement groove 16c, and the motor clutch portion 15 includes an engagement groove 15c. The endoscope clutch portion 16 and the motor clutch portion 15 are always brought into engagement at the constant position with the position regulating surface (4C shown in FIG. 14) serving as the attachment position regulating means formed on the motor unit 4. The tube insertion connector 51 is regulated with respect to the release direction by a pair of fixing members 41 formed on the motor unit 4 for preventing the removal. The detailed separative structure of the detaching portion 14 including the separative conduit 50 will be described later.

When the insertion body 3 is coupled with the motor unit 4 and the tube insertion connector 51 integrated therewith, the endoscope optical connector 17b and the motor optical connector 17a which constitute the optical connector 17 are connected, and the electric contact 3E corresponding to the electric connector 18a is electrically coupled with the electric contact 4B corresponding to the electric connector 18b.

The motor unit 4 is positioned upon its engagement with the tube insertion connector 51 to be fit with the insertion portion engagement portion 3D with the position regulating surface 4C as the attachment position regulating means to be described later, the guide groove 4F, and the connecting surface 4I (see FIG. 14) at the position which makes it sure to engage the endoscope clutch portion 16 with the motor clutch portion 15.

The motor unit 4 is provided with an arm connector 42 on a portion of the upper surface which is capable of detachably fixing the distal end of the arm 5a. The distal end of the arm is fixed to the arm connector 42 such that the endoscope 2 including the motor unit 4 may be held.

The structure of the respective main components of the endoscope 2 will be described in detail.

Figure 9:
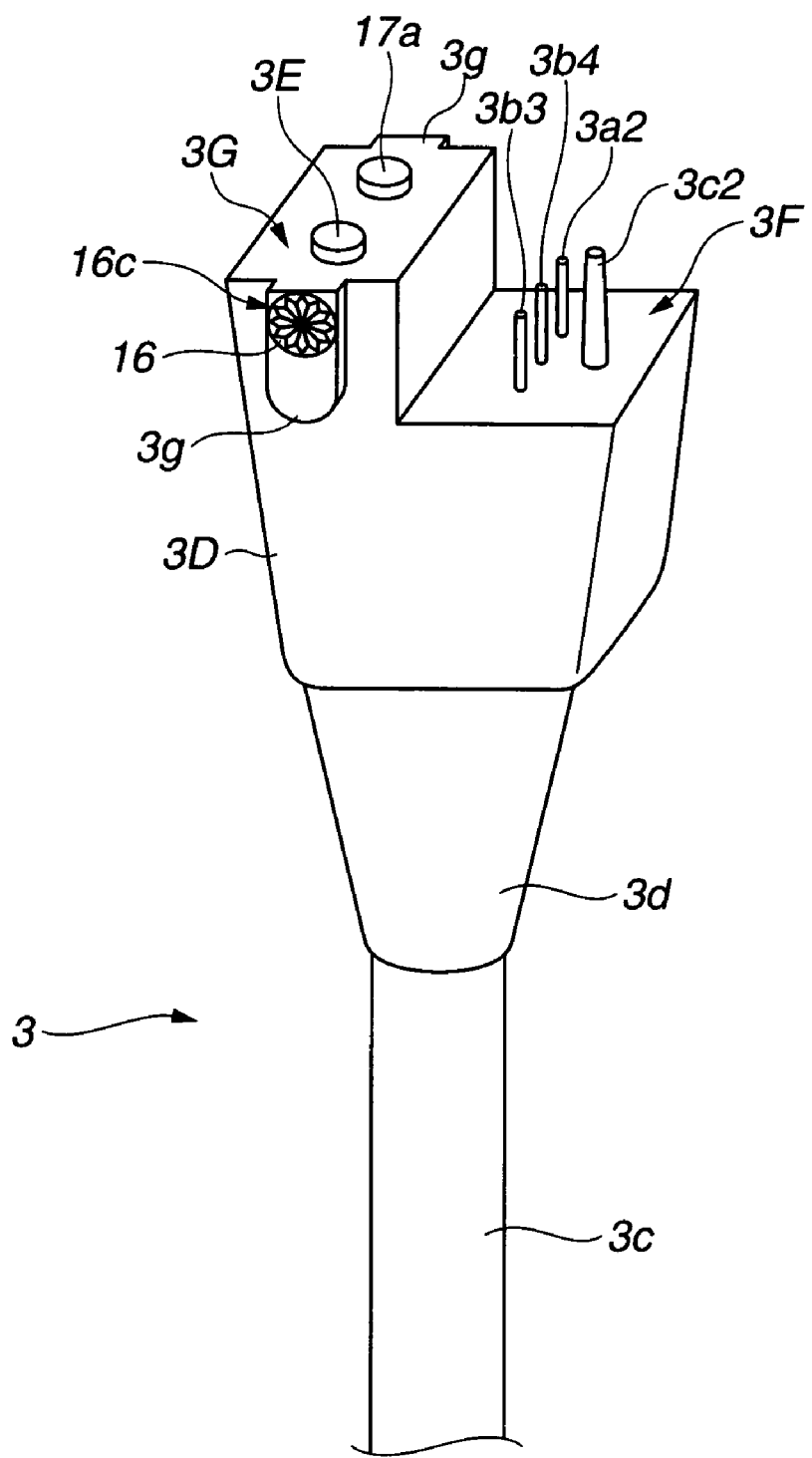
FIG. 9 is an explanatory view showing the structure of the engagement portion of the insertion portion of the insertion body.

Referring to FIG. 9, the insertion portion engagement portion 3D has a notch 3F. The front water supply conduit communication portion 3a2, the air supply conduit communication portion 3b3, the water supply conduit communication portion 3b4, and the suction conduit communication portion 3c2 are provided on the upper surface of the notch portion 3F. The front water supply conduit communication portion 3a2 is communicated with the front water supply conduit 3a1, the air supply conduit communication portion 3b3 is communicated with the air/water supply conduit 3b1, the water supply conduit communication portion 3b4 is communicated with the water supply conduit 3b2, and the suction conduit communication portion 3c2 is communicated with the suction conduit 3c1. Those conduit communication portions 3a2, 3b3, 3b4, and 3c2 are arranged to accommodate the front water supply port 52a, the air supply port 52b, the water supply port 52c, and the suction port 52d provided on the connector surface 52 of the tube insertion connector 51 shown in FIG. 11, respectively.

The endoscope optical connector 17b and the electric contact 3E corresponding to the electric connector 18a are formed on the proximal end surface of the protrusion 3G formed on the insertion portion engagement portion 3D. Engagement guide portions 3g each as the protrusion having the predetermined width and the predetermined height serving as the attachment position regulating means, which is formed on the side surfaces of the protrusion 3G. The engagement guide 3g is structured to be engaged with the guide groove 4F (see FIG. 14) as the attachment position regulating means provided on the motor unit 4 when the insertion portion engagement portion 3D is integrated with the motor unit 4.

The endoscope clutch portion 16 is provided at the predetermined position of the engagement guide portion 3g. The endoscope clutch portion 16 is engaged with the motor clutch portion 15 (FIG. 4) at the motor unit 4 to be described later. In the embodiment, the engagement grooves 15c and 16c provided to the clutch portions 15 and 16 are provided have tooth clutch configurations, having a plurality of grooves arranged at the predetermined pitches along the rotating shaft in the radial direction.

When the insertion body 3 is coupled with the motor unit 4 and the tube insertion connector 51 integrated therewith, the endoscope optical connector 17b and the motor optical connector 17a which constitute the optical connector 17 are connected, and the electric contact 3E corresponding to the electric connector 18a is electrically coupled with the electric contact 4B corresponding to the electric connector 18b.

Figure 10:
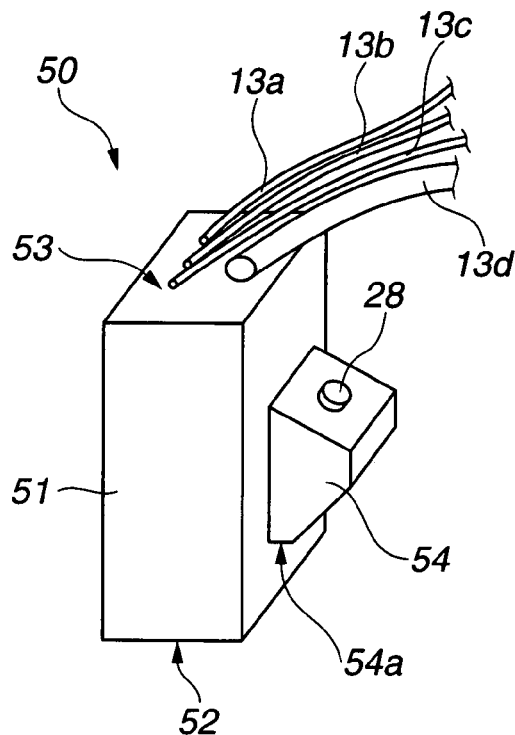
FIG. 10 is an explanatory view mainly showing the structure of the tube insertion connector which forms the separative conduit.

Referring to FIG. 10, the tubes 13a, 13b, 13c, and 13d are communicated with the front water supply port 52a, the air supply port 52b, the water supply port 52c, and the suction port 52d via a through hole corresponding to the front water supply conduit 3a1 (not shown), a through hole corresponding to the air supply conduit 3b1, a through hole corresponding to the water supply conduit 3b2, and a through hole corresponding to the suction conduit 3c1 which are formed in the proximal end surface 53 of the tube insertion connector 51. Referring to FIG. 11, the front water supply port 52a, the air supply port 52b, the water supply port 52c and the suction port 52d are formed in the connecting surface 52 of the tube insertion connector 51, respectively.

Referring to FIG. 10, a protrusion 54 having inclined surfaces is formed on the predetermined surface of the tube insertion connector 51. The forceps insertion opening 28 is formed in the inclined surface of the protrusion 54 to facilitate the operation for inserting the treatment instrument such as the forceps through the forceps insertion opening 28.

Meanwhile, referring to FIGS. 7, 12, 13 and 14, the motor unit 4 includes the first storage portion 4A which detachably stores the tube insertion connector 51, and a second storage portion 4H which detachably stores the insertion portion engagement portion 3D.

The leading end surface of the motor unit 4 is formed as the position regulating surface 4C. The surface of the second storage portion 4H to the back is formed as the connecting surface 4I serving as the attachment position regulating means. Therefore, when the insertion portion engagement portion 3D is fit with the second storage portion 4H, the connecting surface 4I abuts against the proximal end surface of the protrusion 3G, and the notch 3F is partially abuts against the position regulating surface 4C. The endoscope clutch portion 16 is accordingly positioned with respect to the motor clutch portion 15 to make it sure to be engaged. The electric contact 4B corresponding to the electric connector 18b and the motor optical connector 17a are formed in the connecting surface 4I.

An abutment surface 4c against which the reference surface 54a formed on the protrusion 54 is formed on one side surface which constitutes the proximal end opening of the first storage portion 4A. The first storage portion 4A stores the tube insertion connector 51 from the proximal end opening having the bent guide portion 4D. The storage operation is performed in the state where the bottom surface of the tube insertion connector 51 is in tight contact with the standing surface 4a. The tube insertion connector 51 is stored while being abutted against the standing surface 4a and the wall surface 4b of the guide portion 4D. The operation for storing tube insertion connector 51 into the first storage portion 4A is finished by bringing the reference surface 54a of the protrusion 54 into abutment against the abutment surface 4c. In the aforementioned state, the front water supply port 52a, the air supply port 52b, the water supply port 52c, and the suction port 52*d* formed in the connecting surface 52 are connected to the front water supply conduit communication portion 3*a*2, the air supply conduit communication portion 3*b*3, the water supply conduit communication portion 3*b*4, and the suction conduit communication portion 3*c*2 formed in the notch 3F of the insertion portion engagement portion 3D to establish the complete communication states.

The pair of fixing members 41 disposed on the motor unit 4 are plate like members, for example, rotatably held by the respective shafts 41*a*. After storing the tube insertion connector 51 into the first storage portion 4A, the fixing members 41 are disposed on the upper surface of the tube insertion connector 51 as shown in FIG. 7 to make it sure to prevent the removal of the tube insertion connector 51 from the storage portion 4A. The arm connector 42 is interposed between the fixing members 41. The arm portion 5*a* at the leading end of the scope holder 5 is detachably attached to the arm connector 42. The fixing member 41 is not limited to the plate-like member. It may be formed of an arbitrary material into an arbitrary configuration so long as it serves to regulate the tube insertion connector 51 in the removing direction so as to be fixed.

Figure 14:
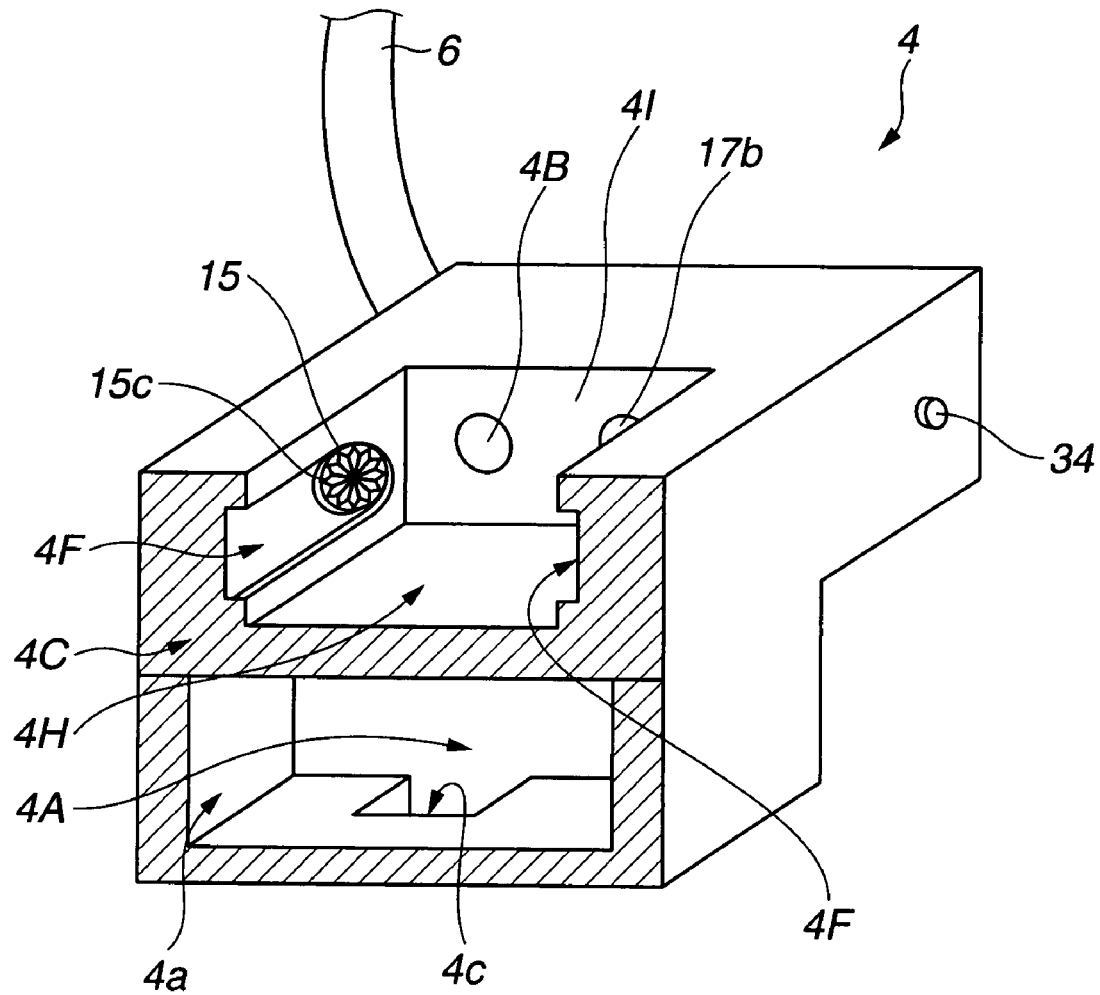
FIG. 14 is a perspective view showing the structure of the motor unit having the first and the second storage portions.

Referring to FIG. 14, guide grooves 4F are formed in the inner wall surfaces at the sides of the second storage portion 4H. The guide groove 4F is engaged with the engagement guide portion 3*g* of the insertion portion engagement portion 3D. The motor clutch portion 15 is disposed on the proximal end of the guide groove 4F. The engagement groove 15*c* having the tooth clutch configuration is formed in the motor clutch portion 15, which is engaged with the engagement groove 16*c* of the endoscope clutch portion 16. Likewise the engagement groove 16*c*, the engagement groove 15*c* includes a plurality of grooves arranged at the predetermined pitches along the rotating shaft in the radial direction.

The engagement/disengagement buttons 34 are formed on both side surfaces of the motor unit 4 for switching between the engagement state and the disengagement state of the motor clutch portion 15 and the endoscope clutch portion 16.

In the embodiment, each of the endoscope clutch portion 16 and the motor clutch portion 15 serving as the first and the second power transmission portions uses the engagement groove 16*c* with the tooth clutch configuration. The present invention is not limited to the structure as described above. They may be formed to have the arbitrary configuration so long as they are reliably engaged as the first and the second power transmission portions to transmit the power.

In the embodiment, the structure having the front water supply conduit 3*a*1 and the water supply conduit 3*b*2 has been described. However, at least one water supply conduit may be provided. In this case, the water supply conduit communication portion 3*b*4 and the water supply tube 13*c* may be provided accompanied with the aforementioned water supply conduits.

The procedure for assembling the endoscope 2 will be described referring to FIGS. 7 to 14.

The operator connects the distal end portion of the arm 5*a* at the leading end which forms the scope holder 5 to the arm connector 42 formed on the motor unit 4 for the purpose of assembling the endoscope 2. The relatively heavy motor unit 4 owing to various electronic parts including the electric motor 23 and the like contained therein may be held by the scope holder 5.

Next, the operator prepares the insertion body 3 which is inserted into the motor unit 4 attached to the scope holder 5, and directs the protrusion 3G of the insertion portion engagement portion 3D opposite the insertion opening of the second storage portion 4H of the motor unit 4. The operator brings the engagement guide portions 3*g* provided at both sides of the protrusion 3G into engagement with the guide grooves 4F of the motor unit 4 so as to confirm the guide state. In the aforementioned guide state, the insertion portion engagement portion 3D is moved toward the connecting surface 4I of the second storage portion 4H. Then the end surface of the protrusion 3G abuts against the connecting surface 4I, and a portion of the plane of the notch 3F of the insertion portion engagement portion 3D abuts against the position regulating surface 4C of the motor unit 4. This allows the insertion portion engagement portion 3D to be stored into the second storage portion 4H of the motor unit 4 in the predetermined state.

In the embodiment, the engagement guide portion 3*g* provided at the protrusion 3G of the insertion portion engagement portion 3D is engaged with the guide groove 4F of the motor unit for storing the insertion portion engagement portion 3D into the second storage portion 4H of the motor unit 4. In addition, when the insertion portion engagement portion 3D is stored in the second storage portion 4H of the motor unit 4, the end surface of the protrusion 3G abuts against the connecting surface 4I of the motor unit 4, and the portion of the plane of the notch 3F abuts against the position regulating surface 4C of the motor unit 4. This makes it sure to place the insertion portion engagement portion 3D in the second storage portion 4H of the motor unit 4 at the predetermined position where the endoscope clutch portion 16 of the insertion portion engagement portion 3D is reliably engaged with the motor clutch portion 15 of the motor unit 4.

The operator depresses the engagement/disengagement button 34 to move the motor clutch portion 15 toward the endoscope clutch portion 16. The engagement groove 15*c* of the motor clutch portion 15 is engaged with the engagement groove 16*c* of the endoscope clutch portion 16 to be ready for the power transmission.

The operator then prepares the separative conduit 50 which is engaged with the first storage portion 4A of the motor unit 4 with which the insertion portion engagement portion 3D is mounted. The bottom surface of the tube insertion connector 51 is disposed on the predetermined surface of the motor unit 4 such that the tube insertion connector 51 of the separative conduit 50 is stored from the proximal end opening of the first storage portion 4A for performing the storage operation.

Then, the tube insertion connector 51 is stored in the first storage portion 4A. In the aforementioned state, the tube insertion connector 51 is further moved such that the front water supply port 52*a*, the air supply port 52*b*, the water supply port 52*c* and the suction port 52*d* formed in the connecting surface 52 are placed opposite the front water supply conduit communication portion 3*a*2, the air supply conduit communication portion 3*b*3, the water supply conduit communication portion 3*b*4, and the suction conduit communication portion 3*c*2 formed in the notch 3F of the insertion portion engagement portion 3D. The tube insertion connector 51 is further moved.

When the reference surface 54*a* of the protrusion 54 abuts against the abutment surface 4*c*, the operation for storing the tube insertion connector 51 into the first storage portion 4A is finished. At this time, the front water supply port 52*a*, the air supply port 52*b*, the water supply port 52*c* and the suction port 52*d* are collectively connected to the front water supply conduit communication portion 3*a*2, the air supply conduit communication portion 3*b*3, the water supply conduit communication portion 3*b*4, and the suction conduit communication portion 3*c*2 through the pressing operation in the predetermined communication state. Thus, the front water supply tube 13*a* is communicated with the front water supply conduit 3*a*1, the air supply tube 13b is communicated with the air supply conduit 3b1, and the water supply tube 13c is communicated with the water supply conduit 3b2 and the suction tube 13d is communicated with the suction conduit 3c1.

Finally, the operator rotates the fixing members 41 of the motor unit 4 around the shaft 41a, and places the fixing members 41 on the upper surface of the tube insertion connector 51 coupled with the motor unit 4. Thus, the tube insertion connector 51 is fixed to the motor unit 4 while being prevented from removing so as to assemble the endoscope 2.

The procedure for separating the endoscope 2 into the insertion body 3, the separative conduit 50, and the motor unit 4 will be described.

The operator confirms that the electric motor 23 is in the stopped state. Then, the operator rotates the fixing members 41 on the motor unit 4 to release the fixed state with the fixing members 41. The tube insertion connector 51 stored in the first storage portion 4A of the motor unit 4 is pulled out. As a result, the tube insertion connector 51 is separated from the motor unit 4.

Next, the operator returns the engagement/disengagement buttons 34 at both side surfaces of the motor unit 4. Then, the shaft of the motor clutch portion 15 engaged with the distal end portion of the engagement/disengagement button 34 is moved in the direction away from the endoscope clutch portion 16. The motor clutch portion 15 and the endoscope clutch portion 16, thus, are disengaged.

Thereafter, the operator grasps the insertion portion engagement portion 3D to be moved downward as shown in FIG. 7. Accordingly, the insertion portion engagement portion 3D is pulled out from the second storage portion 4H of the motor unit 4, that is, the insertion body 3 is separated from the motor unit 4.

The endoscope 2 may be smoothly separated into the insertion body 3, the separative conduit 50, and the motor unit 4 in the reverse procedure for assembling the endoscope 2.

The motor unit 4 is fit with the insertion portion engagement portion 3D provided at the proximal end of the insertion body 3. This makes it possible to reduce the distance between the bending portion 3B and the motor unit 4 to be considerably short. It is possible to transmit the power from the motor unit 4 to the bending portion 3B efficiently. That is, the power transmission loss may be reduced, thus considerably improving the bending performance and the operability.

Also, the relatively heavy motor unit 4 owing to its contained various electronic parts such as the electric motor 23 may be held by the scope holder 5. Therefore, the endoscope 2 may be easily moved to the desired position during the use of the endoscope 2. Thus, the observation and treatment with the endoscope 2 may be sufficiently performed while using the endoscope without exerting specific load to the operator. In addition, the motor unit 4 held by the scope holder 5 is sequentially assembled with the insertion portion engagement portion 3D of the insertion body 3, and the tube insertion connector portion 51 of the separative conduit 50. This may allow the operator to easily perform assembly and disassembly of the endoscope 2. Accordingly, the time required for operation before and after the inspection with the endoscope may be reduced.

The present invention is not limited to the aforementioned embodiment, which may be modified into various forms without departing from scope of the invention.

What is claimed is:

1. A power driven bending endoscope comprising:
an insertion body comprising a bending portion configured to bend; and
a power unit comprising:
a bending drive unit configured to generate a driving force to bend the bending portion, and
a bending state detection unit configured to detect a bending state of the bending portion,
wherein:
the insertion body and the power unit are configured to be detachably coupled,
the insertion body further comprises a first power transmission unit configured to output power from the bending drive unit to the bending portion, and the power unit further comprises a second power transmission unit configured to transmit the power from the bending drive unit to the first power transmission unit, and
the first and second power transmission unit are provided with a first positioning unit and a second positioning unit, respectively, configured to arrange the first power transmission unit to the second power transmission unit to allow an engagement between the first and second power transmission unit at a constant position when the insertion body and the power unit are in a coupled state, and
the power driven bending endoscope further comprises:
an engagement unit configured to operatively engage and disengage the first power transmission unit and the second power transmission unit when the insertion body and the power unit are in a coupled state; and
a separative conduit which is detachably attachable to the insertion body and can communicate with a plurality of tubes disposed in the insertion portion through a single operation, wherein the separative conduit is attachable to the insertion body in a state where the power unit is attached to the insertion body.

2. A power driven bending endoscope with detachable insertion portion according to claim 1, wherein the bending state detection unit includes:
a potentiometer for detecting a displacement of a power transmission unit associated with the bending drive unit; and
an encoder for obtaining a rotating speed and a rotating amount of the bending drive unit.

3. A power driven bending endoscope according to claim 1, wherein the power unit includes a removal prevention unit for preventing removal of the separative conduit.

* * * * *